US00PP32079P2

(12) United States Plant Patent

Carrillo Mendoza et al.

(10) Patent No.: US PP32,079 P2
(45) Date of Patent: Aug. 18, 2020

(54) STRAWBERRY PLANT NAMED 'DRISSTRAWSIXTYEIGHT'

(50) Latin Name: ***Fragaria* x *ananassa***
Varietal Denomination: DrisStrawSixtyEight

(71) Applicant: Driscoll's, Inc., Watsonville, CA (US)

(72) Inventors: Omar Carrillo Mendoza, La Calera (MX); Maribel Martinez Negrete, Watsonville, CA (US); Manuel Lopez, Watsonville, CA (US); Renae R. Robertson, Santa Maria, CA (US)

(73) Assignee: Driscoll's Inc., Watsonville, CA (US)

( * ) Notice: Subject to any disclaimer, the term of this patent is extended or adjusted under 35 U.S.C. 154(b) by 0 days.

(21) Appl. No.: 16/501,602

(22) Filed: May 7, 2019

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
CPC ..... A01H 6/7409
See application file for complete search history.

(56) References Cited

U.S. PATENT DOCUMENTS

PP1,745 P 8/1958 Lang
PP3,981 P 11/1976 Bringhurst et al.
PP4,487 P 11/1979 Bringhurst et al.
PP4,538 P 5/1980 Bringhurst et al.
PP5,262 P 7/1984 Voth et al.
PP5,265 P 7/1984 Voth et al.
PP5,266 P 7/1984 Bringhurst et al.
PP5,300 P 10/1984 Johnson, Jr.
PP5,840 P 12/1986 Johnson, Jr. et al.
PP6,191 P 5/1988 Johnson, Jr. et al.
PP6,231 P 7/1988 Johnson, Jr. et al.
PP6,578 P 1/1989 Voth et al.
PP6,579 P 1/1989 Bringhurst et al.
PP7,024 P 9/1989 Johnson, Jr. et al.
PP7,172 P 2/1990 Voth et al.
PP7,522 P 5/1991 Johnson, Jr. et al.
PP7,614 P 8/1991 Bringhurst et al.
PP7,615 P 8/1991 Bringhurst et al.
PP8,086 P 1/1993 Nelson et al.
PP8,205 P 4/1993 Nelson et al.
PP8,649 P 3/1994 Sjulin et al.
PP8,661 P 3/1994 Bringhurst et al.
PP8,708 P 5/1994 Voth et al.
PP8,745 P 5/1994 Sjulin et al.
PP9,130 P 5/1995 Sjulin et al.
PP9,909 P 6/1997 Ackerman et al.
PP10,221 P 2/1998 Sjulin et al.
PP10,534 P 8/1998 Sjulin et al.
PP10,642 P 10/1998 Amorao et al.
PP11,035 P 8/1999 Mowrey et al.
PP11,277 P 3/2000 Gilford et al.
PP11,279 P 3/2000 Gilford et al.
PP11,522 P 9/2000 Amorao et al.
PP11,548 P 10/2000 Amorao et al.
PP11,554 P 10/2000 Sjulin et al.
PP11,639 P 11/2000 Mowrey et al.
PP12,186 P2 11/2001 Gilford et al.
PP12,436 P2 3/2002 Amorao et al.
PP12,577 P2 4/2002 Amorao et al.
PP12,817 P2 7/2002 Gilford et al.
PP12,899 P2 9/2002 Mowrey et al.
PP13,386 P2 12/2002 Mowrey et al.
PP13,469 P3 1/2003 Larson et al.
PP14,005 P3 7/2003 Amorao et al.
PP14,062 P3 8/2003 Amorao et al.
PP14,109 P3 8/2003 Gilford et al.
PP14,771 P3 5/2004 Amorao et al.
PP15,145 P2 9/2004 Mowrey et al.
PP15,308 P2 11/2004 Sjulin et al.
PP15,375 P2 11/2004 Mowrey et al.
PP15,435 P2 12/2004 Sjulin et al.
PP15,596 P2 3/2005 Amorao et al.
PP15,731 P2 4/2005 Amorao et al.
PP15,752 P2 5/2005 Gilford et al.
PP16,070 P2 10/2005 Gilford et al.
PP16,238 P2 2/2006 Amorao et al.
PP16,241 P2 2/2006 Mowrey et al.
PP16,298 P2 2/2006 Gilford et al.
PP16,299 P2 2/2006 Gilford et al.
PP16,475 P2 4/2006 Gilford et al.
PP16,558 P3 5/2006 López
PP18,000 P2 9/2007 Meulenbroek
PP18,040 P3 9/2007 Mowrey et al.
PP18,041 P3 9/2007 Gilford
PP18,458 P2 1/2008 Ferguson et al.
PP18,575 P3 3/2008 Amorao et al.
PP18,878 P2 6/2008 Mowrey et al.
PP19,240 P2 9/2008 Gilford et al.
PP19,673 P3 2/2009 Ferguson et al.
PP19,767 P2 2/2009 Shaw et al.
PP20,248 P3 9/2009 Rogers et al.
PP20,363 P2 9/2009 Chandler
PP20,701 P2 2/2010 Gilford et al.
PP20,731 P2 2/2010 Mowrey et al.
PP20,733 P2 2/2010 Mowrey et al.
PP20,735 P2 2/2010 Ferguson (Continued)

OTHER PUBLICATIONS

Fear et al., Unpublished U.S. Appl. No. 15/998,014, filed Jun. 11, 2018, titled "Strawberry Plant Variety Named 'DrisStrawFiftyEight'".
Ferguson et al., Unpublished U.S. Appl. No. 15/998,317, filed Aug. 3, 2018, titled "Strawberry Plant Variety Named 'DrisStrawSixty'".
Ferguson et al., Unpublished U.S. Appl. No. 16/501,428, filed Apr. 12, 2019, titled "Strawberry Plant Variety Named 'DrisStrawSeventyFive'".

(Continued)

*Primary Examiner* — Anne Marie Grunberg
(74) *Attorney, Agent, or Firm* — Morrison & Foerster LLP

(57) ABSTRACT

A new and distinct variety of strawberry plant named 'DrisStrawSixtyEight', selected for its high relatively early and late yield, shipping capacity, fruit size, juicy, sweet, aromatic fruit, as well as mite and botrytis field tolerance, is disclosed.

5 Drawing Sheets

(56) References Cited

U.S. PATENT DOCUMENTS

| | | | |
|---|---|---|---|
| PP20,775 | P2 | 2/2010 | Mowrey et al. |
| PP20,922 | P2 | 4/2010 | Gilford et al. |
| PP21,538 | P2 | 11/2010 | Gilford et al. |
| PP21,559 | P2 | 12/2010 | Ferguson et al. |
| PP21,762 | P2 | 3/2011 | Stewart et al. |
| PP22,040 | P3 | 7/2011 | Stewart et al. |
| PP22,218 | P2 | 11/2011 | Ferguson |
| PP22,247 | P2 | 11/2011 | Ferguson |
| PP23,107 | P2 | 10/2012 | Ferguson et al. |
| PP23,148 | P2 | 10/2012 | Gilford et al. |
| PP23,377 | P2 | 2/2013 | Ferguson et al. |
| PP23,378 | P2 | 2/2013 | Pullen et al. |
| PP23,382 | P2 | 2/2013 | Ferguson et al. |
| PP23,383 | P2 | 2/2013 | Ferguson et al. |
| PP23,400 | P2 | 2/2013 | Ferguson et al. |
| PP23,401 | P2 | 2/2013 | Pullen et al. |
| PP23,459 | P2 | 3/2013 | Stewart et al. |
| PP23,506 | P3 | 4/2013 | Ferguson et al. |
| PP23,517 | P3 | 4/2013 | Ferguson et al. |
| PP24,096 | P3 | 12/2013 | Fear et al. |
| PP24,317 | P3 | 3/2014 | Ferguson et al. |
| PP24,333 | P3 | 3/2014 | Vitten et al. |
| PP24,395 | P3 | 4/2014 | Vitten et al. |
| PP24,533 | P3 | 6/2014 | Ferguson et al. |
| PP24,745 | P2 | 8/2014 | Vitten et al. |
| PP25,408 | P3 | 4/2015 | Vitten et al. |
| PP25,437 | P3 | 4/2015 | Vitten et al. |
| PP25,698 | P3 | 7/2015 | Ferguson et al. |
| PP25,699 | P3 | 7/2015 | Stewart et al. |
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| PP27,442 | P2 | 12/2016 | Kibbe et al. |
| PP27,645 | P3 | 2/2017 | Vitten et al. |
| PP27,682 | P3 | 2/2017 | Kibbe et al. |
| PP27,711 | P3 | 2/2017 | Vitten et al. |
| PP27,813 | P3 | 3/2017 | Ferguson et al. |
| PP29,289 | P3 | 5/2018 | Vitten et al. |
| PP29,728 | P2 | 10/2018 | Stewart et al. |
| PP29,729 | P2 | 10/2018 | Kibbe et al. |
| PP29,730 | P2 | 10/2018 | Kibbe et al. |
| PP29,731 | P2 | 10/2018 | Ferguson et al. |
| PP29,747 | P2 | 10/2018 | Vitten et al. |
| PP29,748 | P2 | 10/2018 | Vitten et al. |
| PP29,749 | P2 | 10/2018 | Stewart et al. |
| 2003/0079263 | P1 | 4/2003 | Gilford et al. |
| 2013/0276182 | P1 | 10/2013 | Fear et al. |

OTHER PUBLICATIONS

Jacobs et al. Unpublished U.S. Appl. No. 16/501,501, filed Apr. 18, 2019, titled "Strawberry Plant Variety Named 'DrisStrawSeventy'".

Mendoza et al., Unpublished U.S. Appl. No. 16/350,139, filed Oct. 2, 2018, titled "Strawberry Plant Variety Named 'DrisStrawSixtySeven'".

Mendoza et al., Unpublished U.S. Appl. No. 15/998,020, filed Jun. 12, 2018, titled "Strawberry Plant Variety Named 'DrisStrawSixtyOne'".

Mendoza et al., Unpublished U.S. Appl. No. 15/998,169, filed Jul. 12, 2018, titled "Strawberry Plant Variety Named 'DrisStrawSixtyThree'".

Mendoza et al., Unpublished U.S. Appl. No. 15/998,170, filed Jul. 12, 2018, titled "Strawberry Plant Variety Named 'DrisStrawSixtyTwo'".

Pakozdi et al., Unpublished U.S. Appl. No. 16/501,198, filed Mar. 5, 2019, titled "Strawberry Plant Variety Named 'DrisStrawSeventyThree'".

Pakozdi et al., Unpublished U.S. Appl. No. 15/998,015, filed Jun. 11, 2018, titled "Strawberry Plant Variety Named 'DrisStrawFiftyNine'".

Pakozdi et al., Unpublished U.S. Appl. No. 15/998,028, filed Jun. 14, 2018, titled "Strawberry Plant Variety Named 'DrisStrawSixtyFive'".

Pakozdi et al., Unpublished U.S. Appl. No. 16/501,182, filed Mar. 5, 2019, titled "Strawberry Plant Variety Named 'DrisStrawSeventyFour'".

Pakozdi et al., Unpublished U.S. Appl. No. 16/501,200, filed Mar. 5, 2019, titled "Strawberry Plant Variety Named 'DrisStrawSeventyTwo'".

Stewart et al., Unpublished U.S. Appl. No. 16/350,432, filed Nov. 14, 2018, titled "Strawberry Plant Variety Named 'DrisStrawSixtySix'".

Stewart et al., Unpublished U.S. Appl. No. 15/998,031, filed Jun. 14, 2018, titled "Strawberry Plant Variety Named 'DrisStrawSixtyFour'".

Stewart et al., Unpublished U.S. Appl. No. 16/501,449, filed Apr. 17, 2019, titled "Strawberry Plant Variety Named 'DrisStrawSeventyOne'".

STRAWBERRY PLANT NAMED 'DRISSTRAWSIXTYEIGHT'

Latin name:

Botanical classification: *Fragaria* x *ananassa.*

Varietal denomination: The varietal denomination of the claimed variety of strawberry plant is 'DrisStrawSixtyEight'.

BACKGROUND OF THE INVENTION

Cultivated strawberry is a hybrid species of the genus *Fragaria* that is grown worldwide for its fruit. Modern strawberry was first bred in Brittany, France, in the 18$^{th}$ century by crossing *Fragaria virginiana* with *Fragaria chiloensis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberry is an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

In order to meet these needs, the present invention is directed to an improved variety of strawberry plant. In particular, the invention relates to a new and distinct variety of strawberry plant (*Fragaria* x *ananassa*), which has been denominated as 'DrisStrawSixtyEight'.

Strawberry plant variety 'DrisStrawSixtyEight' originated from a cross between the female parent 'DrisStrawTwentySeven' (U.S. Plant Pat. No. 23,400) and the male parent 'DrisStrawThirtyThree' (U.S. Plant Pat. No. 24,533). Progeny plants from this cross, including 'DrisStrawSixtyEight', were asexually propagated via stolons in McArthur, Shasta County, Calif. in April of 2010. Strawberry plant variety 'DrisStrawSixtyEight' was later specifically identified and selected in Santa Maria, Calif. in November of 2010.

'DrisStrawSixtyEight' was subsequently asexually propagated via stolons, and underwent further testing at a farm in Tapalpa, Mexico for four years (2013 to 2017). The present variety has been found to be stable and reproduce true to type through successive asexual propagations via stolons.

'DrisStrawSixtyEight' exhibits the following distinguishing characteristics when grown under normal horticultural practices in Tapalpa, Mexico:

1. Inflorescence at the same level as foliage
2. Cordate fruit shape; and
3. Partially remontant type of bearing.

'DrisStrawSixtyEight' was selected for its high relatively early and late yield, shipping capacity, fruit size, juicy, sweet, aromatic fruit, as well as mite and botrytis field tolerance.

DESCRIPTION OF THE DRAWINGS

This new strawberry plant is illustrated by the accompanying photographs which show fruit of the plant, flowers, leaves, and plants. The colors shown are as true as can be reasonably obtained by conventional photographic procedures. The photographs are of plants that are one year old.

DETAILED BOTANICAL DESCRIPTION OF THE PLANT

Figure 1:
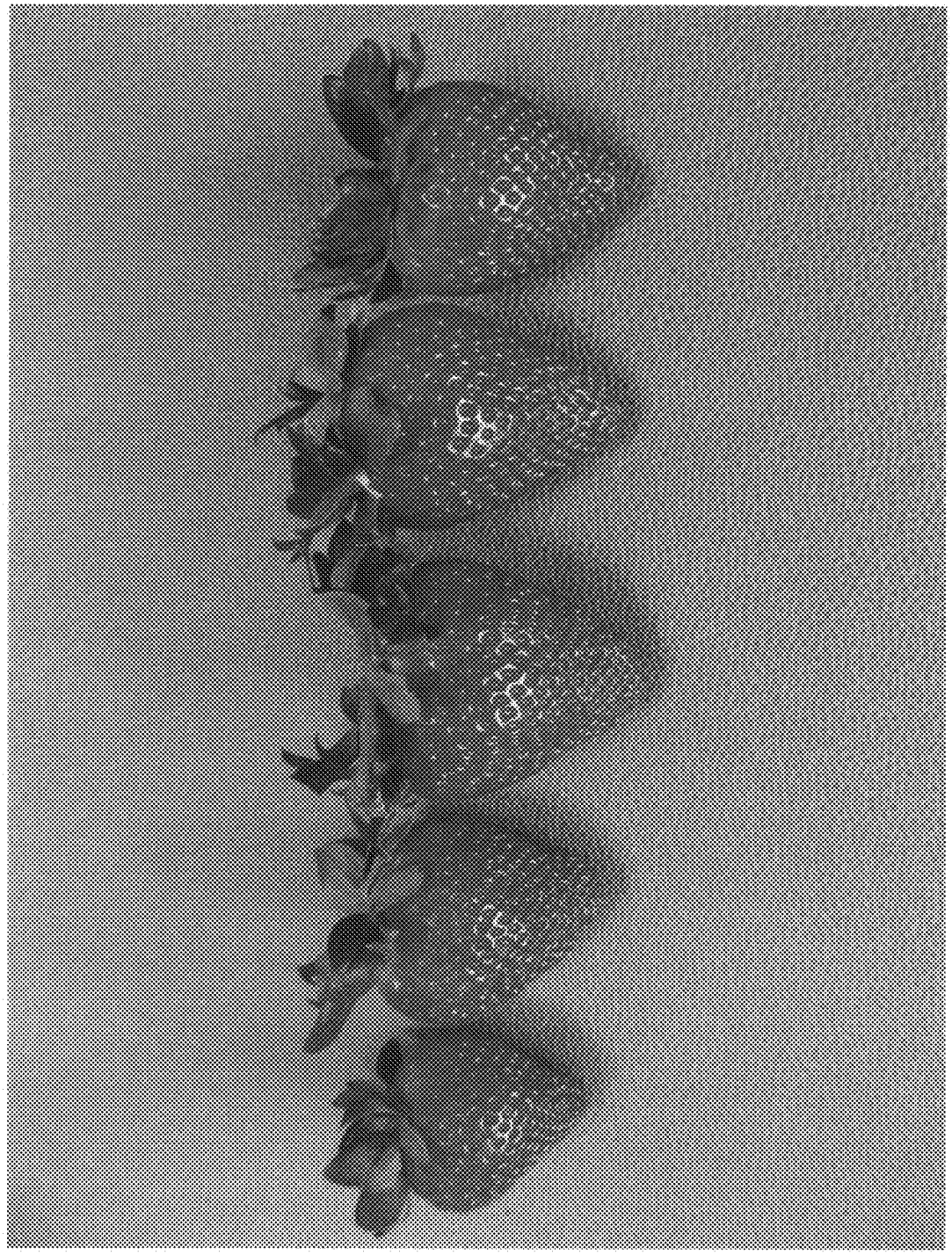
FIG. 1 illustrates whole fruit of variety 'DrisStrawSixtyEight'.
Figure 2:
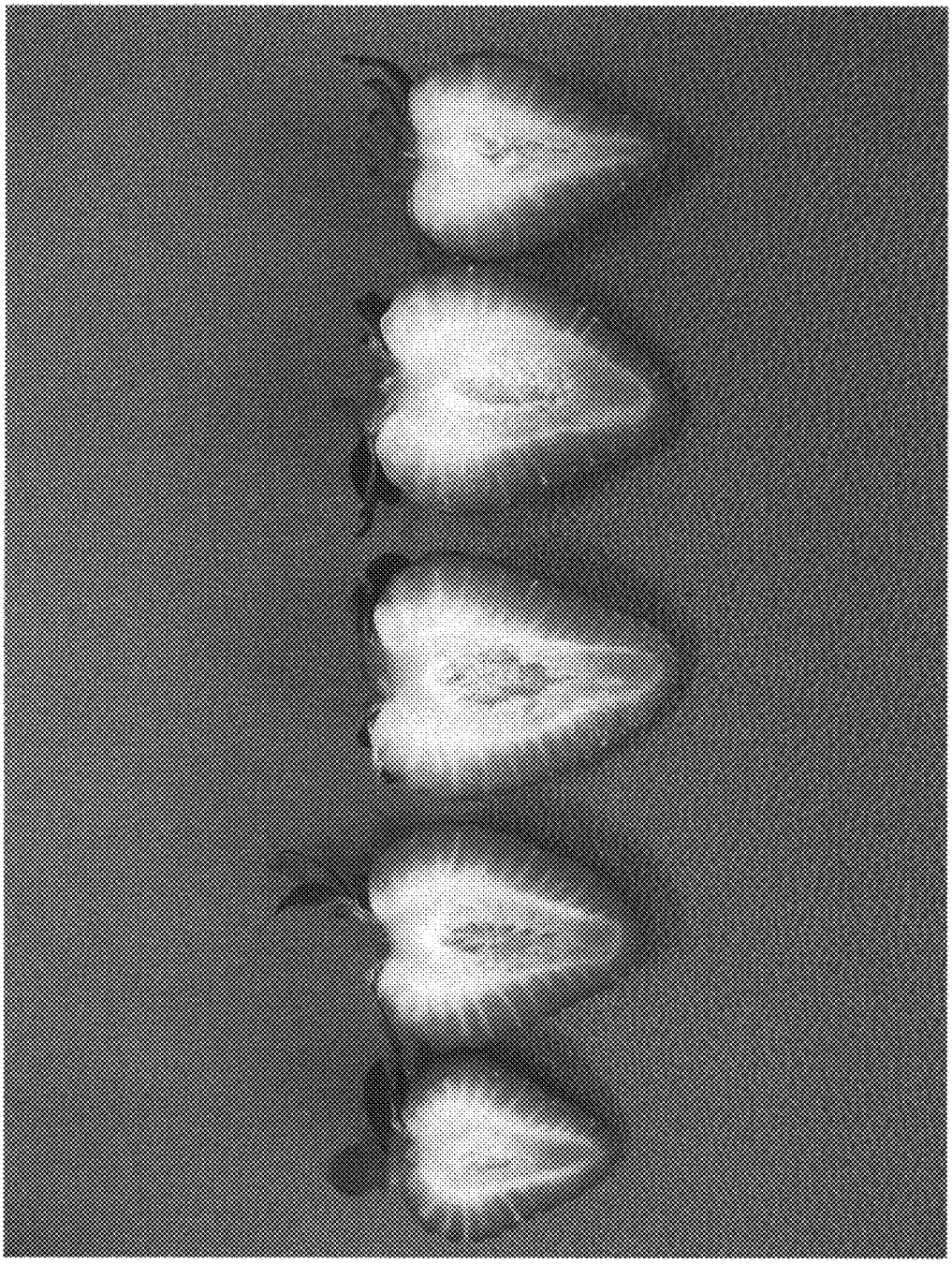
FIG. 2 illustrates longitudinal sections of fruit of variety 'DrisStrawSixtyEight'.
Figure 3:
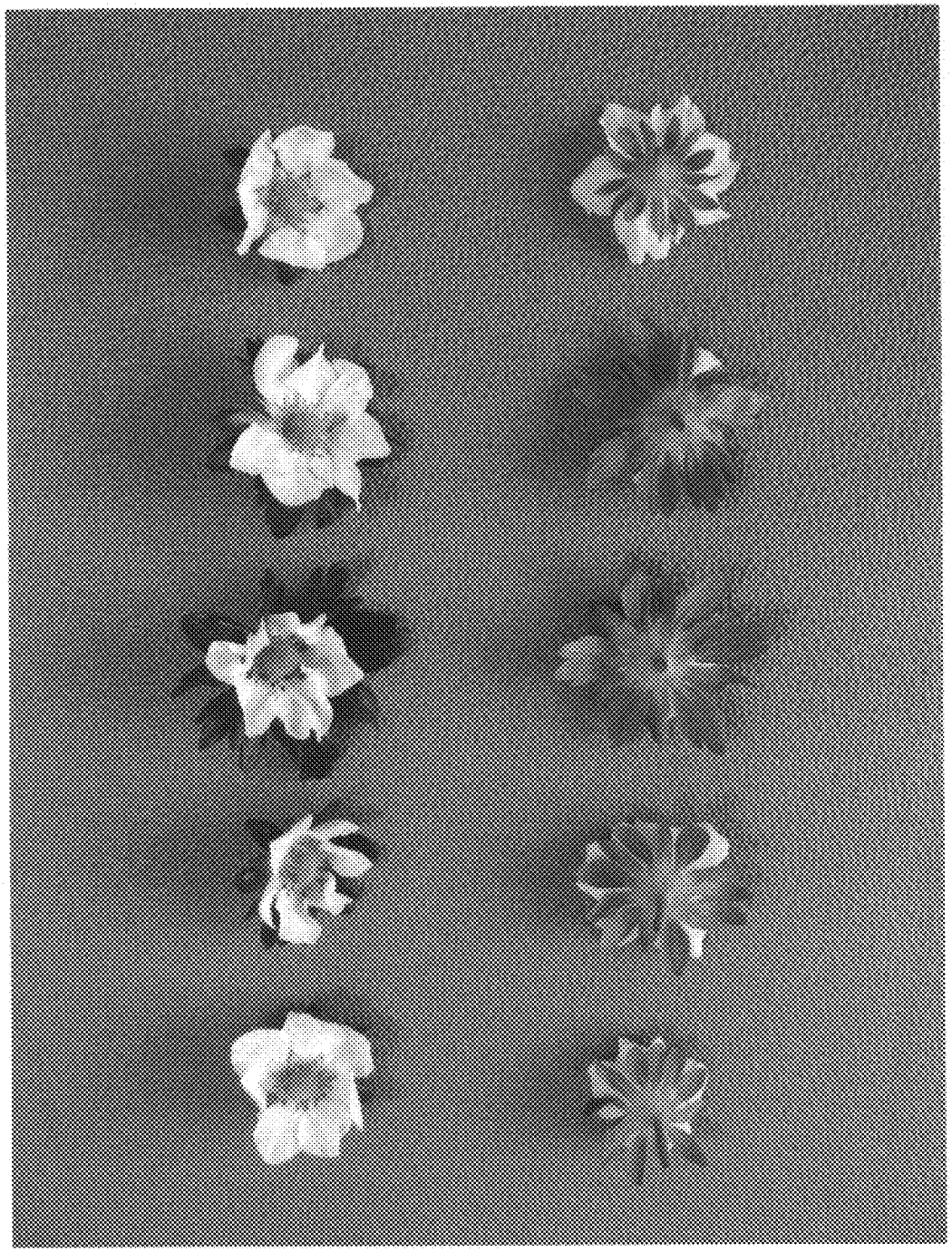
FIG. 3 shows the upper and lower surfaces of flowers of variety 'DrisStrawSixtyEight'.
Figures 4A, 4B:
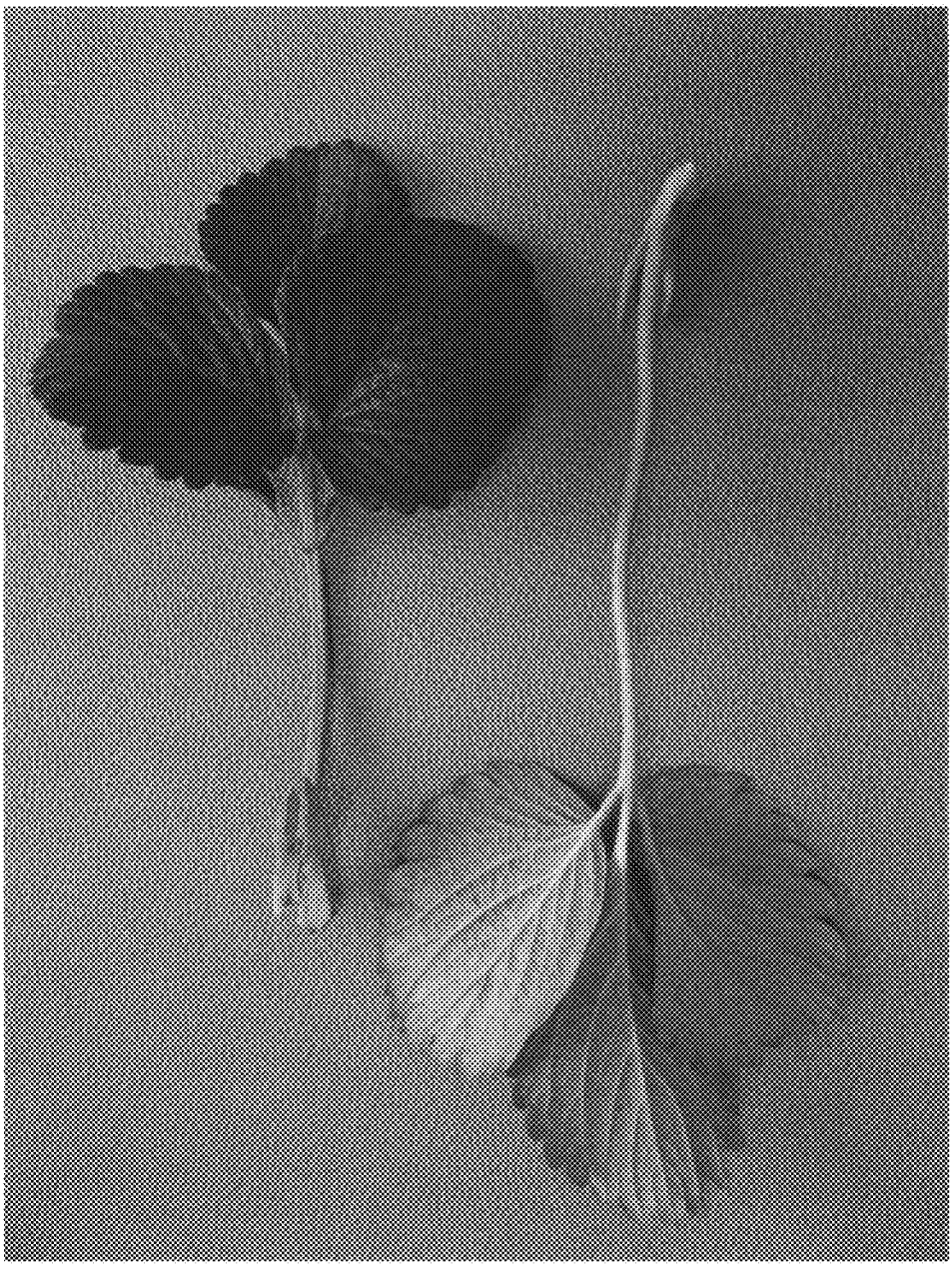
FIG. 4A shows the lower surface of a leaf of variety 'DrisStrawSixtyEight'.
FIG. 4B shows the upper surface of a leaf of variety 'DrisStrawSixtyEight'.
Figure 5:
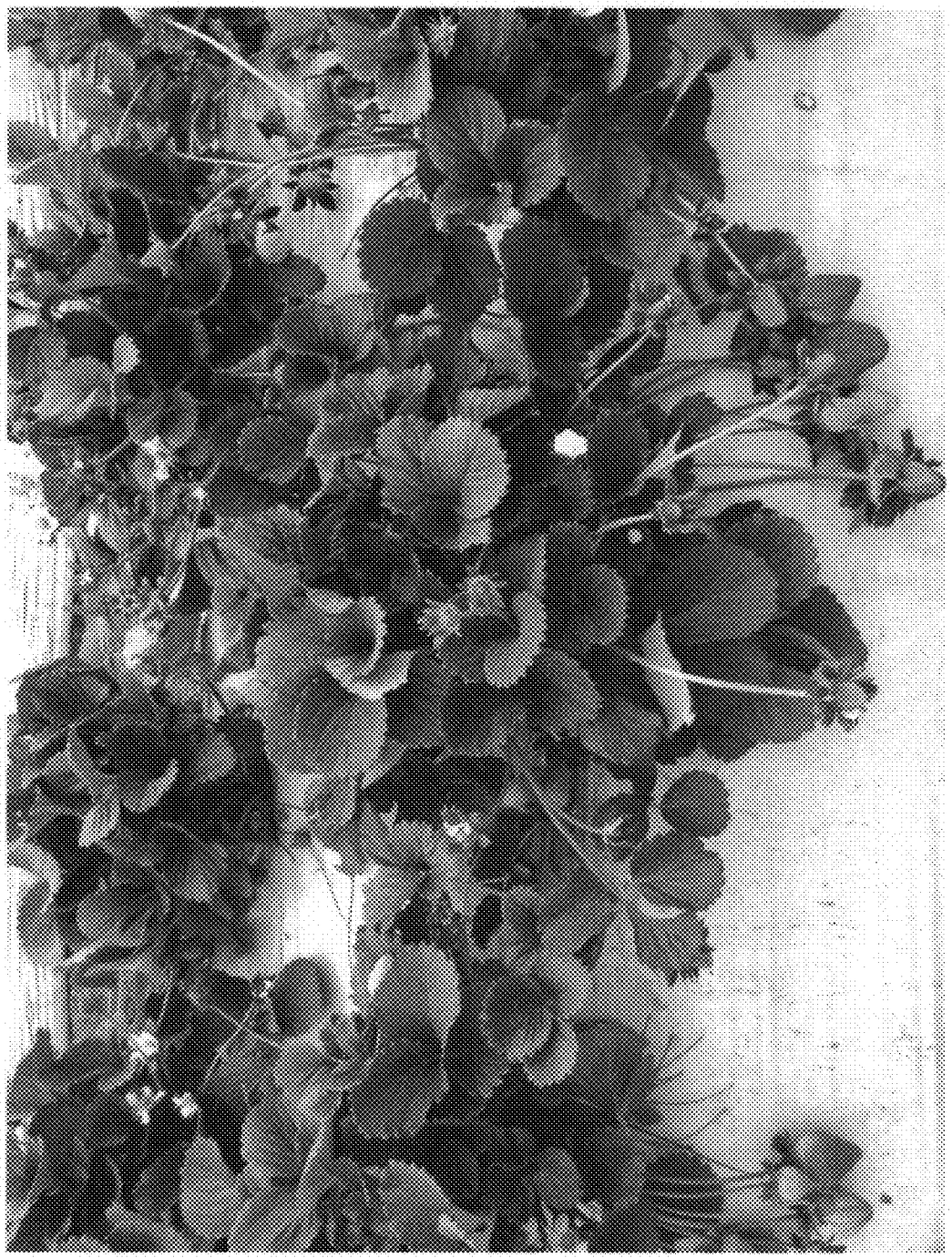
FIG. 5 illustrates plants of variety 'DrisStrawSixtyEight'.

The following detailed descriptions set forth the distinctive characteristics of 'DrisStrawSixtyEight'. The data which define these characteristics is based on observations taken in Tapalpa, Mexico from 2013 to 2017. This description is in accordance with UPOV terminology. Color designations, color descriptions, and other phenotypical descriptions may deviate from the stated values and descriptions depending upon variation in environmental, seasonal, climatic, and cultural conditions. 'DrisStrawSixtyEight' has not been observed under all possible environmental conditions. The botanical description of 'DrisStrawSixtyEight' was taken from plants that were one year old. The indicated values represent averages calculated from measurements of several plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

Classification:

*Species.*—*Fragaria* x *ananassa.*

*Common name.*—Strawberry.

*Denomination.*—'DrisStrawSixtyEight'.

Parentage:

*Female parent.*—The variety 'DrisStrawTwentySeven' (U.S. Plant Pat. No. 23,400).

*Male parent.*—The variety 'DrisStrawThirtyThree' (U.S. Plant Pat. No. 24,533).

Plant:

*Height.*—27.6 cm.

*Diameter.*—32.6 cm.

*Number of crowns per plant.*—5.2.

*Growth habit.*—Semi-upright.

*Density of foliage.*—Medium.

*Vigor.*—Medium.

Stolon:

*Average number of daughter plants per square foot.*—5.

*Diameter at bract.*—3.93 mm.

*Anthocyanin coloration.*—Weak.

*Anthocyanin color.*—RHS 42A (Vivid reddish orange).

*Stolon color*.—RHS 138B (Moderate yellow-green).
*Density of pubescence on the stolon*.—Medium.

Leaf:

*Number of leaflets*.—Three only.
*Color of upper surface*.—RHS 139A (Dark yellowish green).
*Color of lower surface*.—RHS 147B (Moderate yellow-green).
*Leaf blistering*.—Strong.
*Leaf glossiness*.—Medium.
*Variegation*.—Absent.
*Terminal leaflets*.—Length: 6.4 cm. Width: 5.1 cm. Length/width ratio: 1.2. Number of teeth/terminal leaflet: 19. Shape of base: Obtuse. Margin: Serrate to crenate. Shape in cross section: Concave.
*Petiole*.—Length: 11.7 cm. Diameter: 3.8 mm. Attitude of hairs: Slightly outwards. Bract frequency (number present on each petiole): 2. Petiole color: RHS 144C (Strong yellow-green).
*Petiolule*.—Length: 9.5 mm. Diameter: 3 mm.
*Stipule*.—Length: 1.61 cm. Width: 8.4 mm. Anthocyanin coloration: Absent or very weak. Anthocyanin color: RHS 144A (Strong yellow-green). Stipule color: RHS 155A (Pale yellow-green).

Inflorescence:

*Position in relation to foliage*.—Same level.
*Pedicel*.—Attitude of hairs: Slightly outwards. Pedicel color: RHS 144C (Strong yellow-green).
*Flower*.—Flower diameter (petal tip to petal tip on non-flattened flower): 37.9 mm. Arrangement of petals: Overlapping. Stamen: Present. Stamen length: 5 mm. Stamen width: 0.2 mm. Stamen shape: Elongated conic. Stamen color: RHS 145C (Light yellow-green). Number of stamens per flower: 22. Anther color: RHS 13B (Brilliant yellow). Typical and observed number of flowers per plant: 7.8.
*Petal*.—Length: 18.8 mm. Width: 17.6 mm. Length/width ratio: 1.1. Typical and observed petal number: 7.4. Color of upper side: RHS 155C (Greenish white). Color of lower side: RHS 155C (Greenish white).
*Calyx*.—Diameter (sepal tip to sepal tip, measured on back of flower): 44.4 mm. Calyx color: RHS 141B (Deep yellowish green).
*Sepal*.—Length (sepal tip to point of attachment to receptacle): 19.8 mm. Width: 8.8 mm. Typical and observed sepal number: 13.

Fruit:

*Length*.—50.4 mm.
*Width*.—42.4 mm.
*Length/width ratio*.—1.2.
*Fruit hollow length*.—22.9 mm.
*Fruit hollow width*.—11 mm.
*Fruit hollow length/width ratio*.—2.1.
*Shape*.—Cordate.
*Differences in shape between primary and secondary fruit*.—Slight.
*Color*.—RHS 45A (Vivid red).
*Evenness of fruit color*.—Slightly uneven.
*Fruit glossiness*.—Medium.
*Width of band without achenes*.—Medium.
*Fruit firmness*.—Firm.
*Position of achenes*.—Level with surface.
*Achene color*.—RHS 143C (Strong yellow-green).
*Number of achenes per fruit*.—368.
*Achene weight*.—80 mg.
*Peduncle length*.—22 cm.
*Peduncle diameter*.—2.1 mm.
*Number of fruit per truss*.—10.
*Position of calyx attachment*.—Level with fruit.
*Attitude of sepals*.—Outwards.
*Color of flesh* (*excluding core*).—RHS 36A (Light yellowish pink).
*Color of core*.—RHS 34A (Vivid reddish orange).
*Titratable acidity* (*as citric acid in percentage*).—0.3%.
*Sugar content* (*as soluble solids in degrees brix*).—7.8°.

Production:

*Flowering interval*.—Late September to late April.
*Harvest interval*.—Mid-October.
*Type of bearing*.—Partially remontant.
*Productivity*.—41,278 kg to 36,916 kg of fruit per hectare per season from ten-month-old plants when grown in Tapalpa, Mexico.

Resistance to diseases, pests, and abiotic stress:

*Two-spotted spider mite* (*tetranychus urticae*).—Moderately susceptible.
*Botrytis fruit rot* (*botrytis cinerea*).—Moderately susceptible.
*Powdery mildew* (*podosphaera macularis*).—Moderately resistant.

COMPARISON WITH PARENTAL AND COMMERCIAL VARIETIES

'DrisStrawSixtyEight' differs from the female parent 'DrisStrawTwentySeven' (U.S. Plant Pat. No. 23,400) in that 'DrisStrawSixtyEight' has sweeter and juicier fruit and higher yield compared to 'DrisStrawTwentySeven'. Additionally, 'DrisStrawSixtyEight' differs from 'DrisStrawTwentySeven' in that 'DrisStrawSixtyEight' has inflorescence at the same level as foliage, a weak anthocyanin coloration on stolons, a cordate fruit shape, and a partially remontant type of bearing, while 'DrisStrawTwentySeven' has inflorescence above foliage, a strong anthocyanin coloration on stolons, a conical fruit shape, and a not remontant type of bearing.

'DrisStrawSixtyEight' differs from the male parent 'DrisStrawThirtyThree' (U.S. Plant Pat. No. 24,533) in that 'DrisStrawSixtyEight' has inflorescence at the same level as foliage, an obtuse shape of base of terminal leaflet, a cordate fruit shape, and a partially remontant type of bearing, while 'DrisStrawThirtyThree' has inflorescence above foliage, an acute shape of base of terminal leaflet, a conical fruit shape, and a not remontant type of bearing.

'DrisStrawSixtyEight' differs from the commercial variety 'Driscoll El Dorado' (U.S. Plant Pat. No. 16,238) in that 'DrisStrawSixtyEight' has inflorescence at the same level as foliage, an obtuse shape of base of terminal leaflet, a weak anthocyanin coloration on stolons, and a level with the surface insertion of achenes on fruit, while 'Driscoll El Dorado' has inflorescence above foliage, a rounded shape of base of terminal leaflet, a medium anthocyanin coloration on stolons, and a below the surface insertion of achenes on fruit.

'DrisStrawSixtyEight' differs from the commercial variety 'DrisStrawSixtyTwo' (U.S. Plant Pat. No. 31,527) in that 'DrisStrawSixtyEight' has a semi-upright plant growth habit, a serrate to crenate terminal leaflet margin, a cordate fruit shape, and an outwards attitude of sepals on fruit, whereas 'DrisStrawSixtyTwo' has a spreading plant growth habit, a crenate terminal leaflet margin, a cylindrical fruit shape, and an upwards attitude of sepals on fruit.

We claim:

1. A new and distinct variety of strawberry plant named 'DrisStrawSixtyEight' as shown and described herein.

* * * * *